United States Patent [19]

Knoerzer et al.

[11] Patent Number: 5,330,812
[45] Date of Patent: Jul. 19, 1994

[54] SHEET MATERIAL WITH IMPROVED CUT RESISTANCE

[75] Inventors: Anthony R. Knoerzer, Fairport; Pang-Chia Lu, Pittsford; Conway F. Shields, Fairport; Donald G. Whyman, Victor, all of N.Y.

[73] Assignee: Mobil Oil Corp., Fairfax, Va.

[21] Appl. No.: 867,634

[22] Filed: Apr. 13, 1992

Related U.S. Application Data

[63] Continuation-in-part of Ser. No. 611,578, Nov. 13, 1990, abandoned.

[51] Int. Cl.$^5$ .......................... B32B 7/02; B32B 27/16
[52] U.S. Cl. ......................................... 428/40; 428/41; 428/42; 428/220; 428/461; 428/462; 428/475.8; 428/476.3; 428/507; 428/511; 428/516; 428/517
[58] Field of Search ...................... 428/40, 41, 42, 220, 428/461, 462, 475.8, 476.3, 507, 511, 516, 517

[56] References Cited

U.S. PATENT DOCUMENTS 4,888,075 12/1989 Freedman ........................... 428/40

Primary Examiner—Ellis P. Robinson
Assistant Examiner—Nasser Ahmad
Attorney, Agent, or Firm—Alexander J. McKillop; Malcolm D. Keen; Dennis P. Santini

[57] ABSTRACT

A composite material comprising a base liner with a release layer on at least one surface thereof, and a releasable face layer releasably adhered to the base liner through the release layer by a pressure sensitive adhesive, wherein the base liner has a skin layer on its surface proximate to the release layer which is more difficult to cut than the remainder of the base liner material, such that when the composite is subjected to die cutting or perforating to allow portions of the face layer to be selectively removed, the cutter will not penetrate into or through the base liner to any substantial extent.

8 Claims, 1 Drawing Sheet

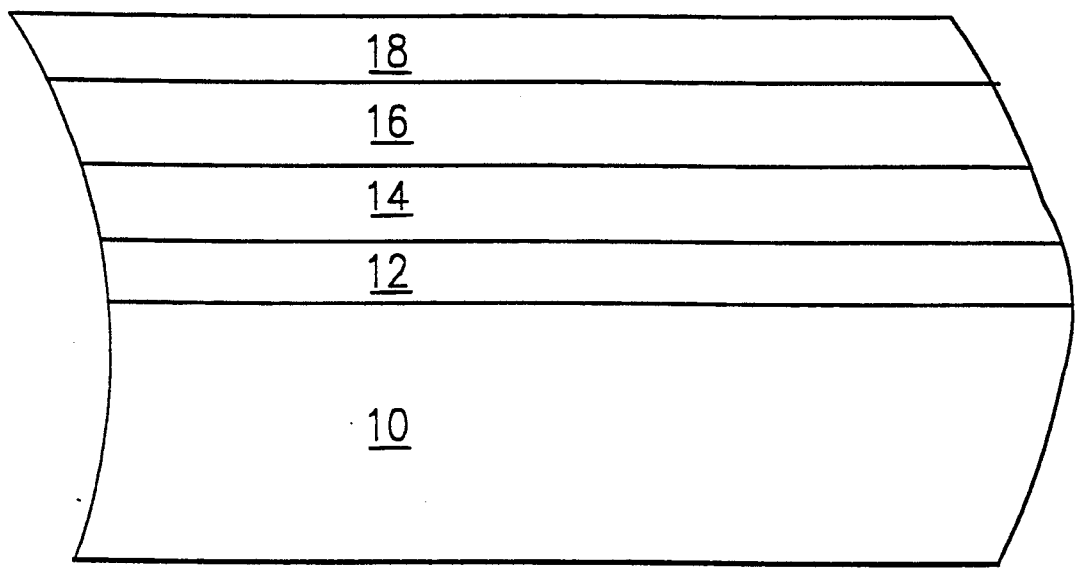

SHEET MATERIAL WITH IMPROVED CUT RESISTANCE

This application is a continuation in part of application Ser. No. 611,578, filed Nov. 13, 1990, now abandoned. The entire contents of that application are incorporated herein by reference.

This invention relates to substrates for use in connection with composite films suitable for the provision of peelable labels having adhesive attached thereto. It more particularly refers to an improved base liner film or sheeting which is to be used as a substrate for such composite films.

BACKGROUND OF THE INVENTION

There is conventionally available composite film form materials comprising peelable self sticking labels, or other similar articles. These are sold commercially with self sticking labels temporarily adhered to a film form base liner substrate. In use, the labels are often preprinted, for example with a person's return address. As needed, each label is peeled from the substrate backing and then permanently affixed to a letter or other appropriate place.

One commercial embodiment of this article uses a multiple layer composite structure comprising a face stock (what will eventually be the label), a pressure sensitive adhesive adhered relatively permanently to the face stock, and a base liner, with a release layer on one side thereof to which the adhesive on the face stock is removably adhered. In the return address illustration set forth above, the return address label would be the face stock. This composite structure is assembled and then passed through a die cutter which has its depth of cut closely controlled so that it cuts the face layer, and the associated adhesive, but not through so much of the base liner/release layer that the die cut severs the base liner as well as the face layer. This allows the later peeling of the labels, which have now been cut from the face layer with pressure sensitive adhesive adhered thereto, from the base liner. When the cut is all the way through the base liner, or even when it is too deep into the base liner, the adhesive may adhere the two layers together with sufficient force to cause the base liner to tear out when peeling the labels is attempted, rather than the adhesive containing labels peeling away from the base liner.

It will be apparent, even from this simple description of this product, that a careful adjustment of the depth of cut, sufficient to achieve what is desired, will be most difficult to accomplish. Thus, it is not uncommon for the base liner to be cut by the die cutting operation, even though efforts are made to carefully control the depth of cut. This can be due to variations in the thickness of the base liner, or of the adhesive layer, or of the face layer, or the die cutting blade. This can also occur as a result of ordinary wear and tear on the machinery which determines the depth of cut.

BROAD STATEMENT OF THE INVENTION

It is therefore an object of this invention to provide novel means for improving the integrity of this system.

It is another object of this invention to provide means to control the die cutting of the face layer of this composite product in a manner which will substantially prevent the cutting of the base liner, or at least limit the cutting of the base liner to an acceptable extent sufficient to allow the labels to be peeled therefrom.

It is a further object of this invention to produce a composite product, of the type described, which has a lower incidence of base liner perforation than was available in the prior art.

Other additional objects of this invention will become apparent from a consideration of this entire specification including the claims appended hereto.

In accord with and fulfilling these objects, one aspect of this invention is to improve the character of a composite article comprising at least a base liner, with a release layer disposed on at least one surface thereof, and a face layer releasable adhered to the release layer on the base liner by means of a pressure sensitive adhesive which is relatively permanently secured to the face layer. This improvement causes fully die cutting out of defined shapes, such as labels, in the face layer, or perforation of the face layer to define such shapes, to be less likely to injure the integrity of the base liner than was possible in the prior art. In making this composite article, the pressure sensitive adhesive is preferably initially adhered to the face layer. However, it is considered to be within the scope of this invention to apply the pressure sensitive adhesive first to the release layer of the base liner. In this case, the pressure sensitive adhesive should transfer to the face layer after the face layer and the base liner have been pressed together.

According to this invention, this improvement is accomplished by changing the character of the base liner so as to change the character of the surface thereof directed toward the face layer, that is the surfaced which is juxtaposed the release layer, and therefore the pressure sensitive adhesive layer, which is more resistant to cutting than is the rest of the film form material from which the base liner has been conventionally made. The important feature of this invention is to make the surface portion of the base liner directed toward the face layer more cut and puncture resistant and therefor to more surely maintain the integrity of the base liner in response to die cutting the face layer and later removal of the shaped areas die cut or perforated therein.

The surface portion of the film being used as the base liner which is being modified according to this invention, may suitably be modified by either changing the inherent character of the surface portion of the film, such as by treatment thereof, or by applying a skin film of the desired character as an overlay onto this surface. Where the base liner surface is being modified by applying a skin layer thereto, this can be accomplished by any of the known techniques, such as for example co-extrusion.

The base liner to be used in this invention is a conventional material. Thus, the base liner can be paper, metal foil, plastic or substantially any other film form material which is suited to the ultimate use to which this product will be put. Typical examples of suitable base liner materials are: polypropylene, polyethylene, polyethylene terephthalate, polystyrene, nylon, polyurethane, other polymeric (plastic) films, paper, metal foils and/or a combination of those materials which have been set forth herein.

The adhesive to be used in the practice of this invention is conventional. It is preferably a pressure sensitive adhesive which adheres more tenaciously to the face layer than it does to the release layer which is disposed on the modified surface of the base liner. Suitable pressure sensitive adhesives for use in the composite article of this invention are well known in this art and can be exemplified by: hot melt adhesives, water based emulsion adhesives, solvent based adhesives, including rubbery adhesives.

The face layer is conventional. It may suitably be a polymeric material. However, as with the base liner, the exact composition of the face layer is not critical to the practice of this invention. The important feature of the face layer is that it serve the purpose of the composite article and that it adhere more strongly to the adhesive than the adhesive adheres to the release layer on the base liner/skin. Suitable face layers include: paper, polyethylene, polypropylene, polyethylene terephthalate, metal foils, laminated composites of these materials, and other similar face stock materials which are per se well known in this trade.

The release layer is conventional. It is a composition which, when applied to the base liner, or to the skin layer disposed on the surface of the base liner, has very low surface tack, and therefore has the ability to readily release materials, particularly pressure sensitive adhesive materials joined to polymeric films, which have been disposed thereon.

In general, those silicone polymers which will release materials overlayed on them are suited to use as a release layer. These polymers are usually curable by conventional means, such as electron beam or ultraviolet radiation, heat, and the like. An example of a conventional release composition which is suited to use in the composite film form material to which this invention is directed is a silicone-acrylate composition. One such composition which is commercially available is an electron beam cured silicone-acrylate copolymer described in the German application PO281681-A1 published by Goldschmidt, AG.

The release layer may suitably be a material which can be applied to the base liner in a rather thin form. The principal characteristics of this material are that it should adhere much more strongly to the base liner than it does to the pressure sensitive adhesive, and the pressure sensitive adhesive should adhere much more strongly to the face layer than it does to the release layer.

DETAILED DESCRIPTION OF THE INVENTION

One way of accomplishing the objectives of this invention is to provide as, or on, the surface of the base liner which will later have the release layer applied thereto, a layer of a relatively soft, flexible polymeric film skin. The thickness of the skin, or of a modified surface layer of the base liner material should be about 2 to 25 microns.

The soft polymer can suitably be any one which is more resistant to being cut or punctured during the die cutting or perforation operations. This material should not be sufficiently brittle to be easily cut by a die cutter, hole puncher, or other knife edge. It can be applied by coextrusion, by lamination, or by coating in the usual manner. It can also be provided by treatment of the surface of the base liner so as to make it tougher and softer, and therefore less likely to be cut by a knife edge. It is also within the scope of this invention to make the surface of the base liner more impact resistant and/or more shear resistant, at the same time as it is being made more cut resistant.

Where a layer of the more cut resistant polymeric material is to be applied onto the surface of the base liner, the means of application are not critical to the practice of this invention. It is important, however, that the polymeric skin be applied in a relatively uniform thickness. While the application of the skin as a strictly uniform layer is not absolutely critical to the practice of this invention, it is desirable for the skin on the base liner not to vary in thickness by more than up to about 5 per cent.

Suitable polymeric skin materials which are more cut resistant than the base liner on which they are disposed include: linear low density polyethylene, high density polyethylene, polyurethanes, polypropylenes and other polymers having similar properties, as well as mixtures of these with each other and with other polymeric materials, such as ethylene-propylene copolymers, ultra low density polyethylene, high impact polystyrene, wax modified polypropylene, and ethylene copolymers, such as ethylene-butene-1 copolymers. The important property of the skin polymer layer of this invention, or of the treated surface of the base liner, is its ability to either resist cutting by a knife edge, particularly a die cutter, or its ability to be uniformly cut so that the cut, if any is made therein, has substantially the same cross-sectional shape and size as the blade making the cut in the face layer. It is believed that this ability, which is important to the practice of this invention, is due to the resiliency and the .impact strength of this material.

The composition of the base liner and of the skin disposed thereon have been set forth herein as being preferably selected from at least one of several materials, respectively. It will be clear that the relationship between the properties of the particularly chosen base liner material and the properties of the particularly chosen skin material are critical to the practice of this invention. These materials must bear a special relationship to each other in that the skin material must be more cut resistant than the base liner material. It will also be clear that not every material in the illustrated examples of materials which are suited to use as base liners or as skin materials, respectively, will be suited to conjoint use. While all of the illustrated materials are suited to be used as stated, they must be used in combination only with another material which satisfies the requirements of this invention, that is that the skin material is more cut resistant than the base liner material.

BRIEF DESCRIPTION OF THE DRAWING

The single FIGURE is an edge cross-sectional view of a portion of a composite sheet according to this invention with a portion of the layers of the sheet broken away.

Referring now to this drawing, the composite article of this invention comprises a base liner 10; a skin layer 12 on at least one surface of the base liner; a release layer 14, which is disposed on at least one surface of the base liner, on the skin; a pressure sensitive adhesive layer 16 disposed on the release layer; and a face layer 18 which is more strongly adhered to the adhesive layer than is the adhesive layer adhered to the release layer. The face layer 18, with the pressure sensitive adhesive adhered thereto is thereby removably adhered to the base liner.

EXAMPLES ILLUSTRATING THE PRACTICE OF THIS INVENTION

Examples 1-5

Several base liner films were produced of oriented polypropylene sheets 2 mils thick. Each was provided with different skin materials, or no skin material in the case of Example 1, as shown in the following table 1. The thickness of the skin was about 12% of the thickness of the entire base liner, and was substantially uniform in thickness across the length and the width of the polypropylene sheet.

Without any adhesive or face stock laminated to them, these samples were evaluated on an Allied Gear Flexomaster model 1B label maker which was set to cut a square shaped label to a depth of one (1) mil, whereby the intent was to compare the relative cut resistance of these samples.

The results of these comparative tests are set forth in the following table 1. In each case the depth of cut was measured at three (3) locations around the cut line: the lead, the trail and the side edges under an optical microscope. The cutting depth is reported as the percentage of the total sheet thickness. The larger the number, the deeper the cut.

TABLE 1

| Sample # | Skin Material | Lead | Trail | Side |
|---|---|---|---|---|
| 1 | none | 22% | 60% | 51% |
| 2 | 50% PP + 50% Kraton-1102 | 14% | 26% | 34% |
| 3 | LLDPE | 19% | 27% | 42% |
| 4 | HDPE | 11% | 32% | 53% |
| 5 | polyurethane | 20% | 29% | 58% |

It is clearly shown that the cut resistance of 2 mil OPP sheet is improved with a soft skin such as PP/Kraton blend, LLDPE, HDPE or polyurethane.

Examples 6-11

Several base liner films were produced of oriented polypropylene sheets 2 mils thick. Each was provided with various skin materials, or no skin material in the case of Example 6, as shown in the following table 2. The skin was about 12 percent of the thickness of the entire base liner thickness, and was substantially uniform in thickness across the length and the width of the propylene sheet. A silicone based release layer was deposited on the skin.

A layer of Findley L3566 water based pressure sensitive adhesive, 20 microns (0.8 mil) thick was deposited on the release layer on the skin side of the base liner by a smooth roll on a Faustel coater, and a layer of Mobil 155R3 polypropylene film, 1.55 mils thick, was laminated over the pressure sensitive adhesive.

These samples were evaluated on the same Allied Gear Flexomaster model 1B label maker as described in Examples 1-5 to cut a depth of 2.75 mils. By this set up, the cutting knife will cut into the base liner of 0.4 mil depth. The cutting depth comparisons listed below are reported as percentages of the base liner thickness.

TABLE 2

| Sample # | Skin Material | Lead | Trail | Side |
|---|---|---|---|---|
| 6 | none | 31% | 54% | 21% |
| 7 | 50% PP + 50% Kraton-1102 | 19% | 32% | 14% |
| 8 | LLDPE | 14% | 51% | 19% |
| 9 | HDPE | 23% | 25% | 9% |
| 10 | ULDPE (ultra low density PE) (Dow Atene-4001) | 28% | 36% | 21% |
| 11 | EP copolymer | 25% | 32% | 11% |

It is shown that the cut resistance of 2 mil OPP sheet is improved with a soft skin such as PP/Kraton blend, LLDPE, LDPE, ULDPE or EP copolymer.

What is claimed is:

1. In a thin film form composite material comprising a base liner film form material, a release layer on at least one surface of said base liner, a pressure sensitive adhesive layer disposed on said release layer, and a peelable face layer film form material disposed on said pressure sensitive adhesive, such that said adhesive layer adheres more strongly to said face layer than to said release layer on said base liner, said face layer being releasable adhered to said release layer on said base liner by means of said adhesive;

the improvement, whereby allowing said composite material to be subjected to a die cutting or perforating operation whereby said face layer and adhesive are cut through so as to make such peelable from said composite, but said base liner is not substantially cut through to an extent such that, if said cut face layer is peeled from said release layer, said base liner retains its integrity, which comprises:

the surface of said base liner adjacent to said release layer being modified to provide a thin and tough skin of polymeric material, comprising up to about 5% in thickness of said base liner, which is more cut resistant than is the remainder of said base liner material to an extent sufficient to maintain the integrity thereof after die cutting of said face layer.

2. A composite material as claimed in claim 1 wherein said base liner comprises at least one material selected from the group consisting of polypropylene, polyethylene, polyethylene terephthalate, polystyrene, nylon, polyurethane, paper and metal foil.

3. A composite material as claimed in claim 1 wherein said face layer comprises at least one material selected from the group consisting of polyethylene, polypropylene, polyethylene terephthalate, and metal foil.

4. A composite material as claimed in claim 1 wherein said skin is at least one material disposed on the surface of said base liner which is selected from the group consisting of ethylene-propylene copolymer, ultra low density polyethylene, high impact polystyrene, wax modified polypropylene, and ethylene-butene-1 copolymer.

5. A composite material as claimed in claim 1 wherein said skin comprises the integral surface layer of said base liner which is modified to make it more cut resistant than the remainder of the base liner.

6. A composite material as claimed in claim 1 including indicia disposed on said face layer.

7. A composite material as claimed in claim 5 wherein said skin layer material is substantially softer than the remainder of said base liner.

8. A composite film form material as claimed is claim 1 wherein said face layer is a peelable label.

* * * * *